United States Patent [19]

Udovich et al.

[11] 4,416,803

[45] Nov. 22, 1983

[54] PROCESS FOR THE MANUFACTURE OF CATALYSTS USEFUL FOR THE OXIDATION OF BUTANE TO MALELIC ANHYDRIDE

[75] Inventors: Carl A. Udovich, Joliet; Eugene H. Hirschberg, Park Forest; Ralph J. Bertolacini, Lisle Township, DuPage County, all of Ill.

[73] Assignee: Standard Oil Company (Indiana), Chicago, Ill.

[21] Appl. No.: 382,181

[22] Filed: May 26, 1982

[51] Int. Cl.$^3$ .............................................. B01J 27/14
[52] U.S. Cl. .................................... 502/209; 502/208; 549/259
[58] Field of Search ................................ 252/435, 437

[56] References Cited

U.S. PATENT DOCUMENTS

| 3,293,268 | 12/1966 | Bergman et al. | 252/437 X |
| 3,385,796 | 5/1969 | Kerr | 252/437 |
| 3,474,041 | 10/1969 | Kerr | 252/437 X |
| 3,832,359 | 8/1974 | Freerks et al. | 252/437 X |
| 3,862,146 | 1/1975 | Boghosian | 549/259 |
| 3,864,280 | 2/1975 | Schneider | 252/435 |
| 3,867,411 | 2/1975 | Roffelson et al. | 252/437 X |
| 3,888,886 | 6/1975 | Young et al. | 252/437 X |
| 3,985,775 | 10/1976 | Harrison | 252/437 X |
| 4,016,105 | 4/1977 | Kerr | 252/437 |
| 4,147,661 | 4/1979 | Higgins et al. | 252/437 X |
| 4,149,992 | 4/1979 | Mount et al. | 252/437 X |
| 4,151,116 | 4/1979 | McDermott | 252/437 X |
| 4,251,390 | 2/1981 | Barone | 252/435 |
| 4,283,288 | 8/1981 | Udovich et al. | 252/437 |

Primary Examiner—William G. Wright
Attorney, Agent, or Firm—Gunar J. Blumberg; William T. McClain; William H. Magidson

[57] ABSTRACT

A process for the manufacture of a phosphorus/vanadium/metal oxide catalyst suitable for the oxidation of butane to maleic anhydride can be prepared by reacting orthophosphoric acid in an aliphatic alcohol and reacting a vanadium compound with an acid and the metal in the aliphatic alcohol to produce the phosphorus/vanadium/metal oxide catalyst.

6 Claims, No Drawings

PROCESS FOR THE MANUFACTURE OF CATALYSTS USEFUL FOR THE OXIDATION OF BUTANE TO MALELIC ANHYDRIDE

BACKGROUND OF THE INVENTION

1. Field of the Invention

The field of this invention relates to processes for the manufacture of phosphorus vanadium and co-metal catalysts suitable for the oxidation of butane to maleic anhydride.

2. Background

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butene is well known and until recently the principal method employed for the manufacture of maleic anhydride was by the air oxidation of benzene in the presence of certain heavy metal oxide catalysts. However, because of the inherent toxicity of benzene fumes, the trend has been to eliminate the utilization of benzene as a feedstock and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; and British Application No. 2,019,839A. While the aforementioned prior art tends to bring about some improvement in the performance of the phosphorus vanadium catalyst there remains much room for improvement, particularly from the standpoint of high conversion, yield and catalyst life.

The object of the present invention is to provide an essentially nonaqueous nonprecipitated method for the manufacture of a phosphorus vanadium and divalent co-metal oxide catalyst for the manufacture of maleic anhydride by the oxidation of butane. A further object is to provide a process for the manufacture of maleic anhydride in the presence of the catalyst manufactured by the novel process.

Our catalyst is, suitably, prepared from an alcoholic solution which has been reacted with orthophosphoric acid, advantageously 100 percent orthophosphoric acid, and has been saturated with another reducing acid suitably gaseous hydrogen chloride. Aliphatic alcohols having 1 to 8 carbon atoms are useful in our process. The preferred alcohols are methanol and ethanol. The acidified alcoholic solution serves both as a reducing agent and as a solvent in our novel process for the manufacture of phosphorus vanadium and co-metal catalysts.

Our catalyst preparation proceeds according to the following reaction sequence:

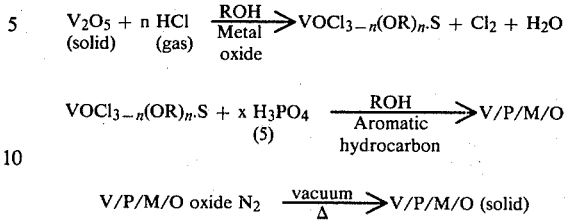

(n = integer 1, 2, 3
S = solvent of solvation

The metal has to be a divalent metal since monovalent metals such as sodium and lithium are not useful in our process. The preferred metals are zinc and molybdenum. The acidified alcohol solution provides a solvent system in which the catalyst system is soluble. In our process for the manufacture of the phosphorus/vanadium/co-metal mixed oxide catalyst, the catalyst does not precipitate from the reaction media. This acidified alcoholic solution provides a solvent system in which the catalyst precursor is soluble. The catalyst is obtained in a quantitative fashion by evaporation of the solvent from the reaction mixture after a suitable period of catalyst development reflux time. While we prefer to use 100 percent crystalline orthophosphoric acid in our process, 96 percent orthophosphoric acid can also be utilized. Our catalyst has a much higher activity than catalysts of the prior art such as those disclosed in U.S. Pat. No. 3,862,146 and U.S. Pat. No. 4,328,126.

The novel catalyst comprises a phosphorus vanadium mixed oxide promoted by a divalent co-metal. Advantageously such a co-metal is either zinc or molybdenum but other metals such as tungsten, uranium and zirconium are also useful in our novel catalyst manufacturing process. The atomic ratio of the vanadium to phosphorus can suitably be in the range of 0.5:1.0 to 1.25:1.0, preferably in the range of 1.0:1.0 to 0.66:1.0. The total atomic ratio of the co-metal to vanadium advantageously is in the range of 0.005:1 to 0.3:1. It is preferred that the total atomic ratio of zinc or molybdenum to vanadium should be in the range of 0.01:1 to 0.25:1. The atomic ratio of phosphorus to vanadium is suitably in the range of 0.8:1 to 2:1, preferably 1:1 to 1.5:1.

Suitably, organic solvents are alcohols or mixtures of alcohols with aromatic hydrocarbons such as orthoxylene. Aliphatic alcohols are usually employed in the process and methanol is the preferred alcohol. Metal such as zinc or molybdenum may be added as a compound together with vanadium or separately introduced into the solution. Suitable zinc or molybdenum compounds comprise metallic zinc, zinc chloride or molybdenum chloride, zinc oxide or molybdenum oxide and most soluble zinc or molybdenum salts. Often it is desirable to improve physical properties of the catalysts, if so the catalysts may be treated with the suspension of an inert support, for example, alumina, titania, silicon carbide, kieselguhr, pumice or silicon. The catalyst may be reinforced with such materials at any stage in its preparation.

According to our process, the average valence of vanadium is in the range of about 3.8 to 4.2. In our catalyst preparation, various anhydrous phosphoric acids may be used in conjunction with orthophosphoric acid; these include pyrophosphoric, triphosphoric acid or meta-phosphoric acid. The vanadium compound can be vanadium pentoxide, vanadium tetrachloride, vanadium trichloride, vanadium oxydichloride, vanadium oxytrichloride, vanadium tetroxide, vanadium oxalate, and most soluble vanadium complexes. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium-containing acids such as metavanadic acid, pyrovanadic acid and the like; vanadium salts such as ammonium metavanadate, vanadium sulfate, vanadium phosphate, vanadyl formate, vanadyl oxalate and the like. However, vanadium pentoxide is preferred.

In the preferred embodiment of our process for the manufacture of the phosphorus/vanadium/molybdenum or zinc oxide catalyst, a vanadium (IV) species is generated in situ by the reduction of $V_2O_5$ with acidic methanol in the presence of a second metal such as molybdenum or zinc and subsequently reacting the catalyst in situ with $H_3PO_4$. Our process recovers 100 percent of the vanadium compared to the usual precipitative processes which recover only 50-70 percent of the vanadium. No precautions are taken to remove water during the reaction to ensure completely anhydrous mixtures. Cost effectiveness is among the many advantages of our novel process for the manufacture of the catalyst. Quantitative use of the expensive vanadium and the use of inexpensive alcohols such as methanol are examples.

This invention also comprises a process for oxidizing butane to maleic anhydride by contacting it in the presence of oxygen with the novel catalyst. The oxidation of butane to maleic anhydride may be accomplished by contacting low concentration of butane in oxygen with the described catalyst. Air is entirely satisfactory as a source of oxygen, but synthetic manufactures of oxygen and diluent gases, such as nitrogen, also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4000 cc of feed per cc of catalyst per hour and more preferably about 1000 to 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury and at 25° C. A variety of reactors will be found to be useful and multiple tube heat exchanger type reactors are quite satisfactory. The tops of such reactors may vary in diameter from about one-quarter inch to about three inches, and the length may be varied from about three to about ten or more feet. The oxidation reaction is exothermic and, therefore, relatively close control of the reaction temperatures should be maintained. It is desirable to have the surface of the reactors at a relatively constant temperature and some medium to conduct heat from the reactors is necessary to aid temperature control. Such media may be Wood's metal, molten sulphur, mercury, molten lead and the like, but it has been found that eutectic salt baths are completely satisfactory. One such salt bath is a sodium nitrate, sodium nitrite-potassium nitrate eutectic constant temperature mixture. An additional method of temperature control is to use a metal block reactor whereby the metals surrounding the tube act as a temperature regulating body. As will be recognized by one skilled in the art, the heat exchanger medium may be kept at the proper temperature by heat exchangers and the like. The reactor or reaction tubes may be iron, stainless steel, carbon steel, nickel, and glass tubes, such as Vycor and the like. Both carbon steel and nickel tubes have excellent long life under the conditions of the reaction described herein. Normally, the reactors contain a preheat zone with an inert material such as one-quarter inch Alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range, which is about 650°-800° F. The oxidation reaction is exothermic and once reaction is underway, the main purpose of the salt bath or other media is to conduct heat away from the reactor tubes and control the reaction. Better operations are normally obtained when the reaction temperature employed is no greater than 20°-50° F. above the salt bath temperature. The temperature of the reactor, of course, will also depend to some extent upon the size of the reactor and the butane concentration.

The reaction may be conducted at atmospheric, at, above or below superatmospheric, or below atmospheric pressure. The exit pressure will be at least slightly higher than the ambient pressure to insure a positive flow from the reaction. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media, with specific operation and purification of the maleic anhydride. The following examples will serve to provide a fuller understanding of the invention, but it is to be understood that these examples are given for illustrative purposes only and will not be interpreted as limiting the invention in any way. In the examples, the terms "conversion," "selectivity" and "yield" are defined as follows:

$$\text{Conversion \%} = \frac{\text{Moles hydrocarbon reacted}}{\text{Moles hydrocarbon in feed}} \times 100$$

$$\text{Selectivity \%} = \frac{\text{Moles maleic produced}}{\text{Moles hydrocarbon feed consumed}} \times 100$$

$$\text{Yield Wt. \%} = (\text{Conversion}) \times (\text{Selectivity}) \times 1.69$$

EXAMPLE 1

To a 2-l, 4-neck flask equipped with mechanical stirrer, reflux condenser, thermometer, submersible gas inlet tube, pressure equalizing funnel and capable of being heated by an electric mantle are charged 500 ml of methanol, 91 g (0.5 gfw) vanadium pentoxide and 4.4 g (0.031 gfw) of molybdenum trioxide. Gaseous hydrogen chloride is introduced by means of the submerged dip leg at such a rate as not to be detected at the condenser outlet. The solution warms to reflux during the addition. The solution becomes homogeneous red-brown in color without any apparent suspended solids present. At this stage the vanadium exists as a mixture of IV and V oxidation states. One hundred and twenty-five grams of crystalline orthophosphoric acid dissolved in 150 ml of methanol are added over fifteen minutes from the pressure equalizing dropping funnel and followed by 200 ml of o-xylene. The solution is brought back to reflux and allowed to reflux 18 hrs. while being stirred. At this stage the solution is a deep blue in color and no solids are evident. Two separate layers are observed. The clear o-xylene upper layer is separated from the lower blue methanol solution and the methanol solution is then filtered to remove about 0.5 g of brown fine textured solids. The methanol solution volume is reduced by distillation to about 200 ml and poured into a teflon dish. The solution is dried overnight in a vacuum oven, at 20 in. vacuum under a nitrogen bleed, at 275° to 350° F. The dried cake developed a brown amorphous dome of material over a deep blue solid bottom. The components were separated by mechanical means and the blue solid was used to prepare the catalyst pellets.

EXAMPLE 2

The deep blue solid from Example 1 is ground and combined with 5 percent by weight of Sterotex and tableted as cored pills, 3/16" diameter external with 1/16" core diameter, at a crush strength of 10 pounds. A 6 cc loading of catalyst was placed in a minireactor under a 1.05 percent butane-synthetic air mixture and heated to 200°–300° F. for 2 hrs. to remove the Sterotex. The catalyst was then evaluated at the desired reaction temperature at the equivalence of 1200–1300 volume hourly space velocity (not adjusted for water pressure) and the results are given in Table I:

TABLE I

| # of pills = 34 | Flow 120 cc/min |
| Wt. of Charge = 4.84 g | Bulk Density = .807 g/cc |
| Vol. of Charge = 6.00 cc | Crush Strength = 10 lb |

| Time on Stream (days) | Temp. | Feed | Conversion Mole % | Selectivity Mole % | Yield Weight % | CO/CO$_2$ | O2 Bal. |
|---|---|---|---|---|---|---|---|
| 0 | | | Bringing up to 760° F. | | | | |
| 1 | 760 | | 39.12 | 65.09 | 43.37 | 2.20 | −1.00 |
| 2 | 800 | 1.087 | 66.08 | 64.02 | 72.05 | 2.08 | −.115 |
| 5 | 801 | 1.068 | 72.34 | 65.38 | 79.92 | 2.05 | −.048 |
| 6 | 801 | 1.061 | 66.24 | 65.52 | 73.35 | 1.98 | +.063 |
| 7 | 823 | 1.061 | 65.63 | 63.46 | 70.39 | 2.10 | −.038 |
| 12 | 824 | 1.063 | 64.51 | 64.14 | 69.92 | 2.05 | −.013 |
| 13 | 829 | 1.060 | 75.43 | 62.39 | 79.53 | 2.07 | −.057 |
| 14 | | | 72.89 | 62.51 | 77.47 | | −.652 |
| 15 | | | 72.97 | 62.00 | 1.45 | 1.16 | −.025 |
| 16 | | | 73.82 | 62.17 | 77.55 | 1.97 | −.020 |
| 19 | | 1.069 | 30.51 | 61.70 | 84.05 | | −.020 |
| 21 | | 1.078 | 51.68 | 62.21 | 35.57 | 1.50 | −.002 |
| 22 | 321 | 1.075 | 30.36 | 61.18 | 54.17 | 1.84 | .038 |
| 23 | 830 | 1.080 | 81.63 | 62.63 | 86.40 | 1.81 | .012 |
| 26 | 830 | 1.081 | 86.42 | 61.44 | 89.73 | 1.68 | .017 |
| 27 | 830 | 1.083 | 87.34 | 60.50 | 89.30 | 1.72 | .019 |
| 27 | 830 | 1.083 | 87.16 | 62.09 | 91.46 | 1.66 | −.034 |
| 27 | 826 | 1.083 | 85.82 | 62.97 | 91.33 | 1.67 | .016 |
| 28 | 824 | 1.053 | 87.71 | 61.86 | 91.69 | 1.58 | .013 |

TABLE I-continued

| # of pills = 34 | Flow 120 cc/min |
| Wt. of Charge = 4.84 g | Bulk Density = .807 g/cc |
| Vol. of Charge = 6.00 cc | Crush Strength = 10 lb |

| Time on Stream (days) | Temp. | Feed | Conversion Mole % | Selectivity Mole % | Yield Weight % | CO/CO$_2$ | O2 Bal. |
|---|---|---|---|---|---|---|---|
| 29 | 819 | 1.077 | 88.53 | 61.72 | 92.35 | 1.56 | .021 |
| 29 | 814 | | 86.54 | 62.74 | 91.76 | | 0.011 |
| 33 | 807 | 1.077 | 86.29 | 64.05 | 93.41 | 1.46 | 0.052 |
| 34 | 806 | 1.079 | 86.76 | 63.05 | 92.45 | 1.54 | 0.005 |
| 35 | 800 | | 85.88 | 63.69 | 92.73 | 1.49 | 0.070 |
| 36 | 806 | 1.075 | 86.89 | 64.09 | 94.12 | 1.50 | 0.002 |
| 37 | 306 | 1.075 | 36.72 | 63.24 | 92.67 | 1.50 | .072 |
| 40 | 804 | 1.081 | 90.10 | 63.53 | 96.73 | 1.51 | −.056 |

The performance of this catalyst after 41 days on stream at 1200 volume hourly space velocity and 804° F. is C S Y (conversion, selectivity, yield) of 90/63.5/96.7 weight percent. This is judged as an excellent performance for a maleic anhydride catalyst under these conditions.

An x-ray analysis of the unused pelleted catalyst material from Example 2 indicates a mixture as follows:

| phase A | 70 percent |
| VO(H$_2$PO$_4$)$_2$ | 13 percent |
| amorphous | 17 percent |

The brown dome material mechanically separated from the blue catalyst and not incorporated in the catalyst tablet had the following analysis:

| phase A | 10 percent |
| amorphous | 90 percent |

An elemental analysis by x-ray fluorescence of the catalyst material is as follows:

| Percent P | 18.8 |
| Percent V | 23.4 |
| Percent Mo | 0.63 |
| P/V/Mo = | 1.32/1/0.014 | and the brown material:

| Percent P | 18.6 |
| Percent V | 22.5 |
| Percent Mo | 0.59 |
| P/V/Mo = | 1.36/1/0.014 |

We claim:

1. A process for the manufacture of a phosphorus/vanadium/metal oxide catalyst wherein the metal has a valence of at least II which is suitable for use in the manufacture of maleic anhydride, which process comprises reacting orthophosphoric acid in an aliphatic alcohol having 1 to 8 carbon atoms and reacting vanadium compound with an acid and the metal in the aliphatic alcohol to produce a phosphorus/vanadium/metal oxide catalyst which is soluble in the media wherein the dissolved phosphorus/vanadium/metal oxide catalyst is solidified by the evaporation of the acidified alcohol and a brown amorphous catalyst precursor is separated from the product and a deep blue phosphorus vanadium oxide catalyst is recovered.

2. The process of claim 1 wherein the vanadium compound is vanadium pentoxide.

3. A process for the manufacture of a phosphorus/vanadium/molybdenum oxide catalyst suitable for use in the manufacture of maleic anhydride from butane which process comprises reacting orthophosphoric acid in an aliphatic alcohol having 1 to 8 carbon atoms and reacting vanadium pentoxide with a molybdenum affording compound and an acid in the aliphatic alcohol to produce an acidified alcohol and a vanadium ester and reacting these to produce a vanadium/phosphorus/molybdenum oxide catalyst dissolved in the acidic alcohol wherein the dissolved phosphorus/vanadium/molybdenum oxide catalyst is solidified by evaporation of the acidified alcohol and a brown amorphous catalyst precursor is separated from the product and a deep blue phosphorus vanadium oxide catalyst is recovered.

4. A process for the manufacture of a phosphorus/vanadium/zinc oxide catalyst suitable for use in the manufacture of maleic anhydride from butane which process comprises reacting orthophosphoric acid in the aliphatic alcohol to produce a vanadium ester and reacting these to produce a vanadium/phosphorus/zinc oxide catalyst dissolved in acetic acid wherein the dissolved phosphorus/vanadium/zinc oxide catalyst is solidified by evaporation of the acidified alcohol and brown amorphous catalyst precursor is separated from the product and a deep blue phosphorus vanadium oxide catalyst is recovered.

5. The process of claim 1 or claim 3 or claim 4 wherein the alcohol is methanol.

6. The process of claim 1 or claim 3 or claim 4 wherein the acid is HCl.

* * * * *